US006534263B1

United States Patent
Plevy et al.

(10) Patent No.: US 6,534,263 B1
(45) Date of Patent: *Mar. 18, 2003

(54) METHODS OF SCREENING FOR CROHN'S DISEASE USING TNF MICROSATELLITE ALLELES

(75) Inventors: Scott E. Plevy, Pacific Palisades, CA (US); Jerome I. Rotter, Los Angeles, CA (US); Stephan R. Targan, Los Angeles, CA (US); Hiroo Toyoda, Arcadia, CA (US); Huiying Yang, Cerritos, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/419,406

(22) Filed: Oct. 15, 1999

Related U.S. Application Data

(63) Continuation of application No. 08/798,668, filed on Feb. 11, 1997, now Pat. No. 6,001,569, which is a continuation of application No. 08/245,297, filed on May 17, 1994, now abandoned.

(51) Int. Cl.⁷ .................. C12Q 15/68; C12P 19/34; C07H 21/04
(52) U.S. Cl. .................. 435/6; 435/91.2; 536/23.1; 536/23.5; 536/24.31; 536/24.33
(58) Field of Search ............ 435/6, 91.2, 810; 536/23.1, 23.5, 24.31, 24.33

(56) References Cited

U.S. PATENT DOCUMENTS 5,225,329 A    7/1993   Marks ............... 435/7.9

FOREIGN PATENT DOCUMENTS

WO       WO 93/07485      9/1992

OTHER PUBLICATIONS

Koutroubakis. Hellenia Journal of Gastroenterology. 8:132–135, 1995.*
Williams et al. BioTechniques. 7:762–768, 1989.*
The Strategene Catalog. p. 39, 1988.*
The Perkin Elmer Cetus Catalog. p. 12, 1992/1993.*
Plevy et al. Gastroenterology. 106:A754, 1994.*

(List continued on next page.)

Primary Examiner—Carla J. Myers
(74) Attorney, Agent, or Firm—Campbell & Flores LLP

(57) ABSTRACT

A novel association between certain tumor necrosis factor microsatellite alleles and Crohn's disease has been discovered. In accordance with the present invention, there is provided methods for screening for Crohn's disease comprising detecting the presence or absence of nucleic acid of a subject encoding TNF microsatellite alleles associated with Crohn's disease, wherein the presence of nucleic acid encoding three or more of the alleles is indicative of Crohn's disease. Kits useful for screening for Crohn's disease are also provided which comprise nucleic acid encoding TNF microsatellite alleles associated with Crohn's disease.

11 Claims, 1 Drawing Sheet

OTHER PUBLICATIONS

Udalova. Genomics. 16:180–186, 1993.*

Figure 1:
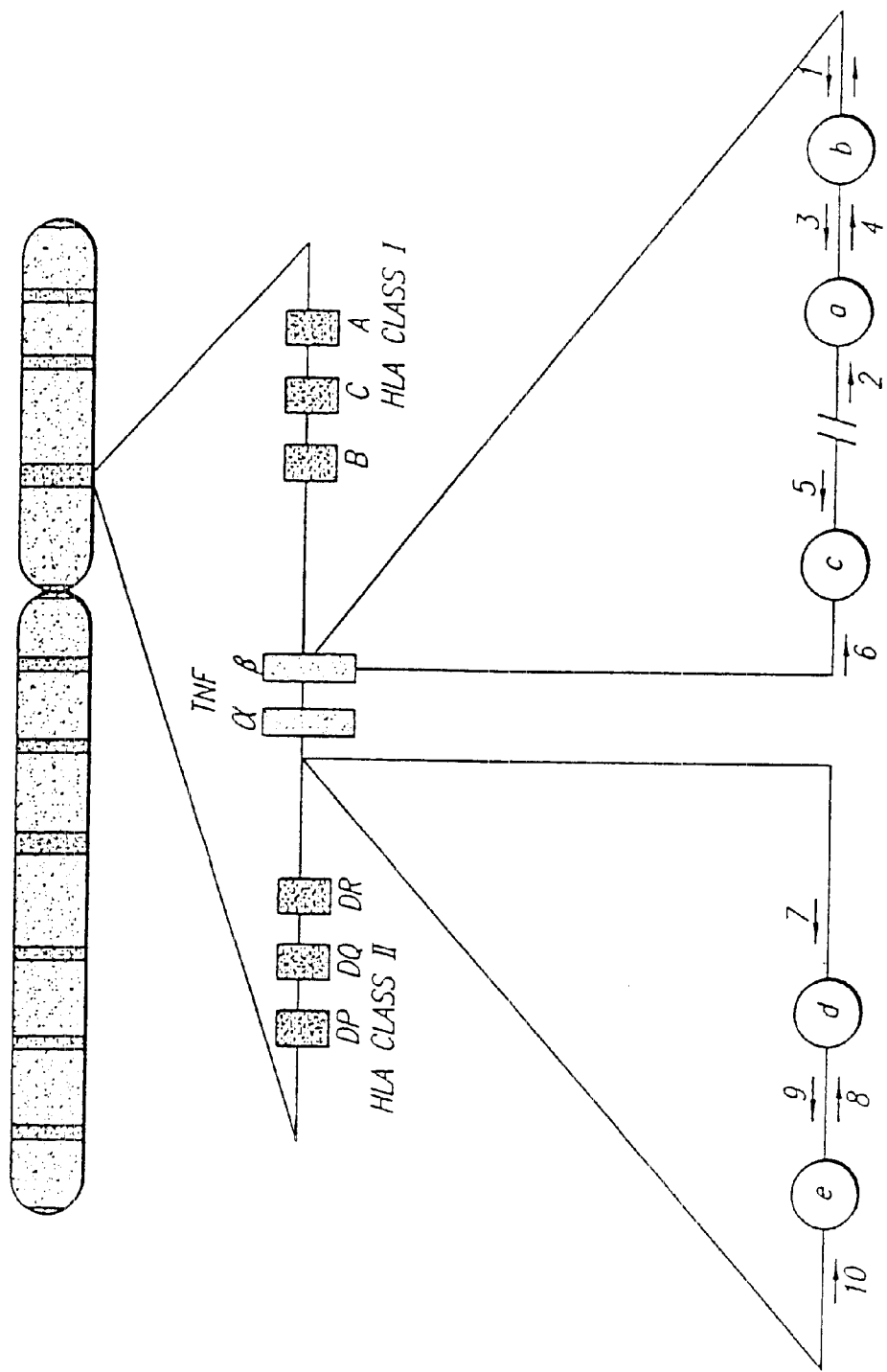

Plevy et al. Gastroenterology. (1995) 108: A895.*

Abraham, L.J., et al., "Haplotypic Polymorphisms of the TNF–β Gene," *Immunogenetics*, 33:50–53 (1991).

Andus, T., et. al., "Measurement of Tumor Necrosis Factor–Alpha mRNA in small numbers of cells by Quantitative Polymerase Chain Reaction," *Regional Immunol.*, 5:11–17 (1993).

Beutler, B., et al., "Control of Cachectin (tumor necrosis factor) Synthesis: Mechanisms of Endotoxin Resistance, "*Science*, 232:977–980 (1986).

Derkx, B., et al., "Tumor–necrosis–factor antibody treatment in Crohn's disease," *Lancet*, 342:173–174 (1993).

Jacob, C.O., et al., "Definition of Microsatellite Size Variants for Tnfa and HSP 70 in Autoimmune and Nonautoimmune Mouse Strains," *Immunogenetics*, 36:182–188 (1992).

Jongeneel, C.V., et al., "Extensive Genetic Polymorphism in the Human Tumor Necrosis Factor Region and Relation to Extended HLA Haplotypes," *Proc. Natl. Acad, Sci. USA*, 88:9717–9721 (1991).

MacDonald, T.T., et al., "Tumor Necrosis Factor–Alpha and Interferon–Gamma Production Measured a the Single Cell Leval in Normal and Inflamed Human Instestine," *Clin. Ext. Immunol.*, 81:301–305 (1990).

McCall, R.D. "Constitutive Expression of TNF–α and of an IL–8 Like Gene is Associated with Genetic Susceptibility to Chronic Granulomatous Etercolitis in Inbred Rats," *Gstroenterology*, 104: No. 4, Part 2 (1993), A740 AGA Abstracts.

Messer, G., et al., "Polymorphic Structure of the Tumor Necrosis Factor (TNF) Locus: An Ncol Polymorphism in the First Intron of the Human TNF–β Gene Correlates With A Variant Amino Acid in Position 26 and A Reduced Level of TNF–β Production," *J. Exp. Med*, 173:209–219 (1991).

Nedospasov, S.A., et al., "DAN Sequence Polymorphism At The Human Turmor Necrosis Factor (TNF) Locus," *J. Immunol.*, 147:1053–1059 (1991).

Partanen, J. et al., "Low Degree of DNA Polymorphismin the HLA–Linked Lymphotoxin (tumor necrosis factor–β) Gene," *Scand J. Immunol.*, 28:313–316 (1988).

Plevy, S.E., et al., "TNF–α mRNA Levels Differentiate Mucosal Inflammation in Crohn's Disease from Ulcerative Colitis," *J. Immunol.*, 150(8):10A (1993).

Pociot, F. et al., "A Tumor Necrosis Factor Beta Gene Polymorphism in Relation to Monokine Secretion and Insulin Dependent Diabetes Mellitus," *Scand J. Immunol.*, 33:37–49 (1991).

Pociot, F. et al., "Association of Tumor Necrosis Factor (TNF) and Class I Major Histopcompatibility Complex Alleles with the Secretion of TNF–α and TNF–β by Human Mononuclear Cells: A Possible Link to Insulin–Dependent Diabetes Mellitus," *Eur. J. Immunol.*, 23:224–231 (1993).

Toyoda, H., et al., "Distinct Associations of HLA Class II Genes With Inflammatory Bowl Diease," *Gastroenterology*, 104:741–748 (1993).

Udalova, I.A., et al., "Highly Informative Typing of the Human TNF Locus Using Six Adjacent Polymorphic Markers," *Genomics*, 16:180–186 (1993).

Webb, G.C., et al., "Genetic Variability at the Human Tumor Necrosis Factor Loci," *J. Immunol.*, 145:1278–1285 (1990).

Yang, H., et al., "Ulcerative Colitis: A Genetically Heterogenous Disorder Defined by Genetic (HLA Class II) and Subclinical (antieutrophil cytoplasmic antibodies) Markers," *J. Clin. Invest.*, 92:1080–1084 (1993).

* cited by examiner

METHODS OF SCREENING FOR CROHN'S DISEASE USING TNF MICROSATELLITE ALLELES

This application is a continuation of U.S. patent application Ser. No. 08/798,668, filed Feb. 11, 1997, U.S. Pat. No. 6,001,569 which is a continuation of U.S. patent application Ser. No. 08/245,297, filed May 17, 1994, abandoned.

I. ACKNOWLEDGEMENT

This invention was made with Government support under grants DK-43211 and DK-46763, awarded by the United States Public Health Service. The Government has certain rights in this invention.

II. FIELD OF THE INVENTION

The present invention relates to methods of screening for inflammatory bowel disease. More specifically, this invention relates to microsatellite alleles in the tumor necrosis factor locus of human chromosome 6 which have been found to be associated with Crohn's disease.

III. BACKGROUND OF THE INVENTION

A. Inflammatory Bowel Disease

Inflammatory Bowel Disease ("IBD") is the collective term used to describe two chronic, idiopathic inflammatory diseases of the gastrointestinal tract: ulcerative colitis ("UC") and Crohn's disease ("CD"). UC and CD are considered together because of their overlapping clinical, etiologic, and pathogenetic features. From a therapeutic and prognostic standpoint, however, it is important to distinguish them from one another as well as from non-chronic inflammatory diseases of the bowel.

IBD occurs world-wide and is reported to afflict as many as two million people. Onset has been documented at all ages; however, IBD predominately begins in young adulthood. The three most common presenting symptoms of IBD are diarrhea, abdominal pain, and fever. The diarrhea may range from mild to severe and is often accompanied by urgency and frequency. In UC, the diarrhea is usually bloody and may contain mucus and purulent matter as well. Anemia and weight loss are additional common signs of IBD. Reports of an increasing occurrence of psychological problems, including anxiety and depression, are perhaps not surprising secondary effects of what is often a debilitating disease that occurs in people in the prime of life.

B. The Cause(s) of IBD are Unknown

Although the cause(s) of UC and CD is not known, there is general agreement that genetics is important in a person's susceptibility to IBD and that the immune system is responsible for mediating the tissue damage in these diseases. Generally speaking, a failure to down regulate the normal self-limited inflammatory response of the bowel is characteristic of IBD. While a wide range of immunologic abnormalities have been reported in these disorders, none has yet been sufficiently reliable to be of diagnostic value. For example, the production of TNF-$\alpha$ by macrophages and T cells of IBD patients is a point of controversy. Although it has been suggested that patients with IBD, particularly CD, exhibit elevated TNF-$\alpha$ protein production and gene expression in the cells of the mucosa, others have not been able to document such a phenomena. Therefore, the diagnostic value of assaying for TNF-$\alpha$ protein production or gene expression is uncertain. Moreover, a suggestion that this immunologic abnormality has a genetic determinant which would be of value in the diagnosis of CD is necessarily speculative in nature.

C. Methods of Diagnosing IBD

A battery of laboratory, radiological, and endoscopic evaluations are combined to derive a diagnosis of IBD and to assess the extent and severity of the disease. Nevertheless, differentiating UC from CD, as well as other types of inflammatory conditions of the bowel, such as irritable bowel syndrome, infectious diarrhea, rectal bleeding, radiation colitis, and the like, is difficult, because the mucosa of the small and large intestines reacts in a similar way to a large number of different insults. Once infectious-types of bowel disorders have been ruled out, the final diagnosis of IBD is often made on the basis of the progression of the disease. In many patients, though, the diagnosis of IBD must still be regarded as indeterminate because of the overlapping features of UC and CD, particularly with CD of the colon.

1. Early Symptoms of IBD

The leading early symptoms of UC and CD are chronic recurrent diarrhea, bloody diarrhea, recurrent abdominal pain, nausea, weight loss general evidence of inflammation without any obvious explanation (fever, raised ESR, leucocytosis, thrombocytosis and dysproteinenemia or anemia). Among these symptoms, diarrhea and anemia are more characteristic of UC while pain, weight loss and marked evidence of inflammation are more common in CD. While the history and physical examination of a patient can help, the final confirmation of the diagnosis has traditionally been made endoscopically, histologically and, in relation to the small intestine, radiologically as well.

2. Endoscopic and/or Radiologic Examination

An endoscopic examination of the bowel can reveal important changes in mucosal appearances which can aid the physician in diagnosing IBD.

Unlike CD, UC is a disease of the mucosa and is confined to the large intestine. UC usually begins in the rectum, although it may involve the entire colon at the time of presentation. When UC spreads, it spreads proximally and continuously, without skipping areas. Hence, it is important to take multiple biopsy specimens from different sites of involved and apparent uninvolved mucosa. In some patients, UC remains localized to the rectum or to the left side of the colon.

The mucosa in acutely active UC appears to be hyperemic, granular and friable, while CD shows lymphoid follicles, aphthoid lesions and flat ulcers. Despite its name, inflammation rather than ulceration is the cardinal feature of UC. Ulcerations may or may not be present in UC. Occasionally, inflammation and ulceration vary in severity in different parts of the colon, including the rectum, giving the false impression of skip areas and rectal sparing, the latter of which are features of CD and are of diagnostic importance for that disorder.

The mucosa of CD exhibits patchy involvement with edema, hyperemia, and ulcerations. The ulceration is a prominent feature of CD. Both superficial and deep undermining or cleft-like ulcers occur. They may be linear or serpiginous. Occasionally, the combination of edema with ulcerations creates a cobblestone appearance that is seen radiologically and endoscopically. Inflammatory polyps, as in UC, may occur.

3. Histological Examination

The cardinal histological features in UC include vascular congestion, edema, goblet cell mucin depletion, crypt abscess formation, and inflammatory cell infiltration of the lamina propria. Crypt abscesses are collections of neutrophils that invade the crypt epithelium and accumulate within the lumen of the crypts. Ulcerations, if they occur, are superficial and only become penetrating to the propria muscularis when the disease is fulminant and acute toxic dilatation of the colon occurs.

Histology in CD shows the characteristic findings of granuloma formation with epithelioid and giant cells. However, these features are found in only 20–40% of biopsies. Transmural inflammation is also typical of CD, and even more typical is its disproportionate distribution (submucosa>mucosa). The mucosa shows infiltration by granulocytes with preservation of normal numbers of goblet cells. Lymphocytes and plasma cells are found in the lamina propria, and lymphoid aggregates are present. Lastly, aphthoid lesions are a typical histological feature in the early stages.

4. Determination of ANCA Status

The presence of anti-neutrophil cytoplasmic antibodies ("ANCAs") can easily be detected in a blood sample, for example, by immunofluorescence assay or a fixed neutrophil ELISA as detailed in Saxon, et al., *J. Allergy Clin. Immunol.*, Vol. 86 No. 2, pp. 202–210 (1990) and incorporated herein by reference. The prevalence of positive ANCA in patients with UC ranges from about 50 to 86%. This UC-associated ANCA has perinuclear immunofluorescence staining pattern which is different from other ANCAs. Moreover, the presence of ANCA is highly specific for UC compared with other forms of colitis. Although a proportion of CD exhibit ANCA, it is at a much lower titre than UC.

Thus the ANCA status of a patient (positive indicating UC and negative indicating CD) is another factor that aids the physician in the diagnosis of IBD. ANCAs also have an increased frequency among the clinically healthy relatives of UC patients compared with environmental and ethnically matched controls. Therefore, ANCA status, in combination with family history of IBD, has also aided physicians in predicting a subject's susceptibility to IBD.

D. Need for Objective Diagnostic Tools

To date most of the diagnostic tools for UC and CD, with the exception of ANCA status, are quite subjective. Diagnosis depends upon a host of procedures aimed at confirming the suspected diagnosis. The initial symptoms are often confused for non-chronic bowel disorders by physicians unfamiliar with IBD. Consequently, IBD often goes mistreated and undiagnosed until the disease shows its chronicity which results in referral of the patient to a specialist. The imprecise and subjective nature of endoscopic and radiologic examination can result in a misdiagnosis between UC and CD or indeterminate diagnosis even when the IBD is suspected.

Histological examination does provide greater certainty of an accurate diagnosis, but the problems of differentiating between the two diseases based on the histological findings are often underestimated. There is no single histological criterion which is proof of one or the other disease. The epithelial cell granuloma for example, which is often accorded a key role in the diagnosis of CD is only to be found in about 20% of biopsy specimens from such patients. They can also occur in other diseases. Unfortunately, the patient must often suffer as the disease progresses before a definitive diagnosis can be made.

The selective identification of CD as opposed to UC or other inflammatory conditions of the intestines carries important prognostic and therapeutic implications. For example, when colectomy is indicated, the type of IBD involved determines which surgical options are appropriate. Surgery (total colectomy) does represent a cure in UC, though a dramatic one. In CD, surgery is never curative. Continent procedures such as the ileorectal pull-through (mucosal proctectomy) or the Kock pouch may be desirable in UC, but are contraindicated in CD.

The availability of a genetic marker that would readily distinguish CD from UC and/or non-chronic inflammatory diseases of the bowel, independent of or in combination with existing diagnostic tools, would represent a major clinical advance which would aid in therapeutic management of IBD and the design of more specific treatment modalities. Accordingly, there has existed a need for convenient and reliable methods of screening for CD and distinguishing CD from UC for diagnostic, prognostic and therapeutic purposes.

IV. BRIEF DESCRIPTION OF THE INVENTION

A novel association between Crohn's disease ("CD") and the presence of specific microsatellite alleles at the tumor necrosis factor ("TNF") locus of human chromosome 6 has been discovered. This association provides the basis for convenient and reliable methods of screening for CD and distinguishing CD from ulcerative colitis ("UC").

In accordance with the present invention, there is provided methods of screening for CD comprising detecting the presence or absence of nucleic acid of a subject encoding TNF microsatellite alleles associated with CD, wherein the presence of nucleic acid encoding two or more of the alleles is indicative of CD. TNF microsatellite allele associated with CD include the a2, b1, c2, d4 and e1 TNF microsatellite alleles. Preferably, CD is indicated by the detection of nucleic acid encoding TNF microsatellite alleles associated with CD including the a2, b1, and c2 TNF microsatellite alleles. More preferably, nucleic acid is detected which also encodes the d4 or e1 TNF microsatellite alleles, or both.

Nucleic acid encoding TNF microsatellite alleles associated with CD may be detected in accordance with the present invention by amplifying the nucleic acid and identifying the TNF microsatellite alleles. TNF microsatellite allele may be identified by assaying nucleic acid of a subject for defining characteristics of TNF microsatellite alleles associated with CD and comparing the results to a positive and or negative control. Defining characteristics of nucleic acid encoding TNF microsatellite allele associated with CD include, for example, size, sequence, type of sequence repeats, and the like. Primers suitable for use in amplifying nucleic acid encoding TNF microsatellite alleles are provided herein.

Also provided are methods of screening for CD which comprise determining the TNF microsatellite alleles encoded by nucleic acid of a subject at TNF microsatellite loci selected from the group consisting of a, b, c, d and e, and identifying CD by the presence of three or more TNF microsatellite alleles selected from the group consisting of a2, b1, c2, d4 and e1.

Kits for screening for CD and for distinguishing CD from UC are also described which comprise nucleic acid encoding TNF microsatellite alleles associated with CD, for example, the a2, b1, c2, d4 and e1 TNF microsatellite alleles. Kits of the present invention may also include reagents, primers, sequencing markers, positive and negative controls and the like, which are useful in the practice of the present invention.

V. BRIEF DESCRIPTION OF THE DRAWING

FIG. 1 is a schematic of the TNF microsatellite loci as they map (not to scale) at the TNF loci in chromosome 6.

TNF microsatellite alleles are designated by lettered circles PCR primer location and orientain with regard to TNF microsatellite loci is indicated by numbered arrows. The numbered arrows correspond with SEQ ID NOS 1 through 10.

VI. DETAILED DESCRIPTION OF THE INVENTION

An association between Crohn's disease ("CD") and the presence of specific microsatellite alleles at the tumor necrosis factor ("TNF") locus of human chromosome 6 has been discovered. This association provides the basis for convenient and reliable methods of screening for CD, providing physicians with valuable information in the diagnosis of IBD and the determination of susceptibility to CD.

The human TNF locus consists of two tandemly arranged and closely linked genes encoding two pleiotropic cytokines: tumor necrosis factor (TNF-α) and lymphotoxin (TNF-β) together with flanking sequences. The TNF locus is located within the major histocompatibility complex (MHC) and maps centromeric to HLA-B and telomeric to the class III region.

Recently an abundant class of DNA polymorphisms at the human TNF locus, referred to herein as TNF microsatellites, were mapped, characterized and reported in Nedospasov, S. A., et al. *J. Immunology*, 147: 1053–1059 (1991); Jongeneel, C. V., et al., *Proc. Natl. Acad. Sci.*, 88: 9717–9721 (1991); Udalova, I. A., et al. *Genomics*, 16: 180–186 (1993), and Pociot, F., et al., *European J. Immun.*, 23: 224–231 (1993), each of which are incorporated herein by reference in their entirety. These TNF microsatellites are characterized by a series of CA/GT or CT/GA dinucleotide sequence repeats. The function of these TNF microsatellites are presently unknown.

Five TNF microsatellite loci have been mapped and characterized. TNF microsatellite a and TNF microsatellite b are closely linked and located 3.5 kb upstream of the TNF-β gene. The TNF microsatellites a and b are characterized by CA/GT dinucleotide sequence repeats. TNF microsatellite c is located within the intron of the TNF-β gene and is characterized by CT/GA dinucleotide sequence repeats. TNF microsatellite d and TNF microsatellite e are located 8 to 10 kb downstream of the TNF-α gene. TNF microsatellite d is characterized by TC/GA-like sequence repeats. TC/GA-like sequence repeats are similar to TC/GA repeats except that the TC/GA repeats are interrupted by an extra base pair. TNF microsatellite e is characterized by TC/GA dinucleotide sequence repeats. FIG. 1 depicts a map of the TNF microsatellite loci at the TNF locus. For a more detailed description of the TNF microsatellite loci and the TNF locus, see, Nedospasov, S. A., et al., *J. Immunol.* 147: 1053–1059 (1991); Jongeneel, C. V., et al., *Proc. Natl. Acad. Sci. USA* 88: 9717–9721 (1991); and Udalova, I. A., et al., *Genomics* 16: 180–186 (1993), each of which are incorporated by reference herein in their entirety.

Each TNF microsatellite has two or more alleles. TNF microsatellite alleles of a single locus are differentiated by the number of consecutive sequence repeats. Provided herein are also size characteristics of the TNF microsatellite alleles determined from and relative to amplification nucleic acid of the cell lines identified in Udalova, et al., *Genomics* 16: 180–186 (1993) (incorporated by reference herein) and deposited with the American Society of Histocompatibility and Immunogenics ("ASHI") with the Center for Human Polymorphism Studies ("CEPH") in accordance with Example 2 below.

TNF microsatellite a is presently known to have thirteen alleles referred to herein as the a1, a2, a3, a4, a5, a6, a7, a8, a9, a10, a11, a12, and a13 TNF microsatellite alleles. Each one of the TNF microsatellite a alleles has a characteristic number of CA/GT dinucleotide sequence repeats and a characteristic size as determined from the cell lines and the amplification technique noted above. Table 1 lists the name, type of sequence repeat, number of sequence repeats and characteristic size of each TNF microsatellite a alleles. This information may be confirmed and the specific sequence of the alleles, including their flanking regions may be determined by sequencing amplified nucleic acid of the cell lines as noted above.

TABLE 1

TNF microsatellite a alleles by name, the type of sequence repeat, the number of sequence repeats and the size.

| NAME OF ALLELE | SEQUENCE REPEATS | NUMBER OF REPEATS | SIZE IN BASE PAIRS |
|---|---|---|---|
| a1 TNF microsatellite allele | CA/GT | 6 | 98 |
| a2 TNF microsatellite allele | CA/GT | 7 | 100 |
| a3 TNF microsatellite allele | CA/GT | 8 | 102 |
| a4 TNF microsatellite allele | CA/GT | 9 | 104 |
| a5 TNF microsatellite allele | CA/GT | 10 | 106 |
| a6 TNF microsatellite allele | CA/GT | 11 | 108 |
| a7 TNF microsatellite allele | CA/GT | 12 | 110 |
| a8 TNF microsatellite allele | CA/GT | 13 | 112 |
| a9 TNF microsatellite allele | CA/GT | 14 | 114 |
| a10 TNF microsatellite allele | CA/GT | 15 | 116 |
| a11 TNF microsatellite allele | CA/GT | 16 | 118 |
| a12 TNF microsatellite allele | CA/GT | 17 | 120 |
| a13 TNF microsatellite allele | CA/GT | 18 | 122 |

TNF microsatellite b is presently known to have seven alleles referred to herein as the b1, b2, b3, b4, b5, b6 and b7 TNF microsatellite alleles. Each one of the TNF microsatellite b alleles has a characteristic number of CA/GT dinucleotide sequence repeats (8 to 20 repeats) and a characteristic size as determined from the cell lines and the amplification technique noted above. Table 2 lists the name, type of sequence repeat, number of sequence repeats and size of each TNF microsatellite b alleles. This information may be confirmed and the specific sequence of each allele, including its flanking regions may be determined by sequencing amplified nucleic acid of the cell lines as noted above.

TABLE 2

TNF microsatellite b alleles by name, the type of sequence repeat, the number of sequence repeats and the size.

| NAME OF ALLELE | SEQUENCE REPEATS | NUMBER OF REPEATS | SIZE IN BASE PAIRS |
|---|---|---|---|
| b1 TNF microsatellite allele | CA/GT | 8 | 123 |
| b2 TNF microsatellite allele | CA/GT | 9 | 125 |
| b3 TNF microsatellite allele | CA/GT | 10 | 127 |
| b4 TNF microsatellite allele | CA/GT | 11 | 129 |
| b5 TNF microsatellite allele | CA/GT | 12 | 131 |
| b6 TNF microsatellite allele | CA/GT | 13 | 133 |
| b7 TNF microsatellite allele | CA/GT | 14 | 135 |

TNF microsatellite c is presently known to be biallelic. The two alleles of TNF microsatellite c are referred to as the c1 TNF microsatellite allele and the c2 TNF microsatellite allele. The c1 TNF microsatellite allele is 160 base pairs in size and is further characterized by a series of nine CT/GA dinucleotide sequence repeats. The c2 TNF microsatellite allele is 162 base pairs in size and is characterized by a series of ten CT/GA dinucleotide sequence repeats. This information may be confirmed and the specific sequence of the alleles, including their flanking regions, determined by sequencing amplified nucleic acid of cell lines as noted above.

TNF microsatellite d is presently known to have seven alleles referred to herein as the d1, d2, d3, d4, d5, d6 and d7 TNF microsatellite alleles. Each one of the TNF microsatellite d alleles has a characteristic number of CT/GA-like dinucleotide sequence repeats and a characteristic size. Table 3 lists the name, type of sequence repeat and characteristic size of each TNF microsatellite d alleles. The number of sequence repeats and specific sequence of the TNF microsatellite alleles may be determined and the size of the alleles confirmed by sequencing amplified nucleic acid of cell lines as noted above.

TABLE 3

TNF microsatellite d alleles by name, the type of sequence repeat, the number of sequence repeats and the size.

| NAME OF ALLELE | SEQUENCE REPEATS | SIZE IN BASE PAIRS |
| --- | --- | --- |
| d1 TNF microsatellite allele | CT/GA-like | 124 |
| d2 TNF microsatellite allele | CT/GA-like | 126 |
| d3 TNF microsatellite allele | CT/GA-like | 128 |
| d4 TNF microsatellite allele | CT/GA-like | 130 |
| d5 TNF microsatellite allele | CT/GA-like | 132 |
| d6 TNF microsatellite allele | CT/GA-like | 134 |
| d7 TNF microsatellite allele | CT/GA-like | 136 |

TNF microsatellite e is presently known to have four alleles. The four alleles of TNF microsatellite e are referred to as the e1 TNF microsatellite allele, the e2 TNF microsatellite allele and the e3 TNF microsatellite allele and the e4 TNF microsatellite allele. The e1 TNF microsatellite allele is 99 base pairs in size and is characterized by a series of CT/GA sequence repeats. The e2 TNF microsatellite allele is 101 base pairs in size and is further characterized by a series of CT/GA sequence repeats. The e3 TNF microsatellite allele is 103 base pairs in size and is characterized by a series of CT/GA sequence repeats. The e4 TNF microsatellite allele has not yet been identified in humans, but is 105 base pairs in size and is characterized by a series of CT/GA sequence repeats. The number of sequence repeats and specific sequence of the TNF microsatellite alleles may be obtained and the size of the alleles confirmed by sequencing amplified nucleic acid of cell lines as noted above.

In accordance with the present invention, there is provided methods of screening for Crohn's disease comprising detecting the presence or absence of nucleic acid of a subject encoding TNF microsatellite alleles associated with Crohn's disease, wherein the presence of nucleic acid encoding two or more of the alleles is indicative of Crohn's disease.

The term "nucleic acid" as used herein refers to DNA and RNA derived from a single chromosome. In presently preferred embodiments, the methods and kits of the invention employ DNA and even more preferably genomic DNA. Nucleic acid of a subject which is suitable for screening in accordance with the present invention may be derived from any nucleated cell sample, and preferably from peripheral mononuclear blood cells.

The phrase "TNF microsatellite alleles associated with Crohn's disease" as used herein refers to alleles of the TNF microsatellite loci which are found to be in haplotypic association with one another in a population of persons having CD and include, for example, the a2 TNF microsatellite allele, the b1 TNF microsatellite allele, the c2 TNF microsatellite allele, the d4 TNF microsatellite allele and the e1 TNF microsatellite allele. Other TNF microsatellite alleles associated with Crohn's disease may be identified by (1) determining the TNF microsatellite alleles encoded at the TNF microsatellite loci of a population of persons having CD and a population of persons not having CD and (2) identifying those TNF microsatellite alleles which occur on the same chromosome with greater frequency in the population of persons having CD than in the population of persons not having CD. Haplotypic association can then be confirmed by selecting a person from the population having CD who is identified as having nucleic acid encoding TNF microsatellite alleles associated with CD and determining that one or more of this person's parents also has the same TNF microsatellite alleles associated with CD.

In accordance with the present invention, the presence of nucleic acid encoding two or more TNF microsatellite alleles associated with CD is indicative of CD. The presence of nucleic acid encoding three or more TNF microsatellite alleles associated with CD is a preferable indication of CD. Even more preferably, the detected nucleic acid encodes TNF microsatellite a2, TNF microsatellite b1, and TNF microsatellite c2. Still more preferably, the nucleic acid detected also encodes the d4 TNF microsatellite allele or the e1 TNF microsatellite allele. Most preferably, nucleic acid is detected that encodes the a2 TNF microsatellite allele, the b1 TNF microsatellite allele, the c2 TNF microsatellite allele, the d4 TNF microsatellite allele and the e1 TNF microsatellite allele.

Detecting the presence or absence of nucleic acid of a subject encoding TNF microsatellite alleles associated with CD may be accomplished by determining whether or not nucleic acid of a subject encoding a TNF microsatellite possesses a defining characteristic of nucleic acid encoding TNF microsatellite alleles associated with CD. One of skill in the art will understand that there are many means available to make such a determination, e.g., electrophoresis, automated sequencing, allele-specific oligonucleotide probing, differential restriction endonuclease digestion, ligase-mediated gene detection, and the like.

For example, isolated nucleic acid encoding a TNF microsatellite can be assayed for such characteristics as size, specific sequence, type of sequence repeats, number of sequence repeats, ability to hybridize with a labeled probe under specific hybridization parameters, ability to hybridize with an antibody specific for a particular allele and the like, and then compared to a positive control which defines the same characteristic for a known TNF microsatellite allele associated with CD and/or a negative control which defines the same characteristic for a TNF microsatellite allele not known to be associated with CD.

The presence of nucleic acid of a subject encoding TNF microsatellite alleles associated with CD can be detected by identifying nucleic acid encoding TNF microsatellite alleles having the same defining characteristics as nucleic acid encoding TNF microsatellite alleles associated with CD or by identifying nucleic acid encoding TNF microsatellite alleles having different defining characteristics than nucleic acid encoding TNF microsatellite alleles not known to be associated with CD or by a combination of both techniques.

For example, a positive control for a TNF microsatellite allele associated with CD is the c2 TNF microsatellite allele which characteristically has 10 CT/GA sequence repeats. A negative control for a TNF microsatellite allele associated with CD would be the c1 TNF microsatellite allele which characteristically has 9 CT/GA sequence repeats. Nucleic acid of a subject can be assayed to determine the number of CT/GA repeats at the TNF microsatellite c locus. Using the c2 TNF microsatellite allele as a positive control, the presence of nucleic acid of a subject encoding a TNF microsatellite allele associated with CD would be detected if nucleic acid was identified that encodes 10 CT/GA sequence repeats, like the c2 TNF microsatellite allele. Using the c1 TNF microsatellite allele as a negative control, the presence of nucleic acid of a subject encoding a TNF microsatellite allele associated with CD would be detected if nucleic acid encoding 10 CT/GA sequence repeats, was identified, unlike the c1 TNF microsatellite allele. However, the greatest likelihood of accurately detecting the presence of a TNF microsatellite allele associated with a CD at the TNF microsatellite c locus of the subject being tested is to compare the results of the assay to the positive and negative control.

When all five TNF microsatellite loci are being assayed to detect the presence or absence of TNF microsatellite alleles associated with CD, a convenient positive control is the BSM cell line, deposited with the ASHI under accession number 9032 and with the CEPH under accession number WS68. Additional positive and negative controls are available in the form of cell lines containing nucleic acid encoding known TNF microsatellite alleles are described by name, accession number and encoded TNF microsatellite allele in Udalova et al., *Genomics,* 16:180–186 (1993), incorporated herein by reference in its entirety.

To increase the accuracy of detecting TNF microsatellite alleles, the control should be subjected to the same test procedures and parameters as the nucleic acid of the subject being assayed. Likewise, assays to detect the presence or absence of nucleic acid encoding TNF microsatellite allele associated with CD should be calibrated against a standard. For example, in a presently preferred embodiment using size as the defining characteristic of TNF microsatellite alleles associated with CD, a positive control (a nucleic acid sequence known to encode a TNF microsatellite allele associated with CD) is amplified and electrophoresed using the same reagents, primers and parameters as that used for the nucleic acid of the subject being tested. A sequencing marker equal in size to the control is also subjected to electrophoresis using the same reagents and parameters as those used with the test and control nucleic acid. Sequencing markers useful in the practice of the present invention are available from a variety of commercial sources, including pGEM-3Zs(+) control DNA available from Promega, Inc. of Madison, Wis.

Nucleic acid of a subject encoding one or more TNF microsatellites can be amplified to make detection of TNF microsatellite alleles associated with CD easier. Amplification of nucleic acid may be achieved using conventional methods, see, e.g., Maniatis, et al., Molecular Cloning: A Laboratory Manual 187–210 (Cold Spring Harbour Laboratory, 1982) which is incorporated herein by reference. Amplification, however, is preferably accomplished via the polymerase chain reaction ("PCR") method disclosed by U.S. Pat. Nos. 4,698,195 and 4,800,159, the respective contents of which are incorporated herein by reference. Application of PCR to detect microsatellites requires less DNA and is faster than standard Southern blotting and hybridization techniques.

Thus, oligonucleotide primer pairs can be constructed that allow enzymatic amplification of a subject's nucleic acid that encodes one or more TNF microsatellites. The amplified nucleic acid can then be assayed to detect the presence or absence of TNF microsatellite alleles associated with CD.

Primer pairs suitable for use in the practice of the present invention are linear oligonucleotides ranging in length from about ten to about thirty nucleotides in length. One of the primers in the pair should be complementary to a nucleotide sequence upstream of the nucleic acid encoding the TNF microsatellite targeted for amplification. The other primer should be complementary to a sequence located down stream of this target site. Preferably, the primers suitable for use in the present invention are specific for amplification of nucleic acid encoding TNF microsatellites and do not prime amplification of nucleic acid which does not encode TNF microsatellites.

The sequences complementary to the primer pairs may be separated by as many nucleotides as the PCR technique and the other technique(s) for detecting the presence or absence of TNF microsatellite allele associated with CD will allow, provided that an appropriate control is used. For example, if the presence or absence of nucleic acid of a subject encoding TNF microsatellite allele associated with CD is detected on the basis of size, then the primers used for amplification must not include amplification of nucleic acid flanking the allele which would interfere with the ability to detect polymorphic size differences (by inclusion, for example, of polymorphic size differences which may be present in regions flanking the TNF microsatellite alleles).

Primers suitable for use in amplifying nucleic acid encoding TNF microsatellite alleles can be constructed using the oligonucleotide primer sequences described herein, the cell lines described in Udalova, I.A., et al., *Genomics,* 16:180–186 (1993) (incorporated herein by reference) and deposited with the ASHI and the CEPH, and the map and sequence of the TNF locus available from Genebank as part of the human genome project funded through the National Institute of Health and incorporated herein by reference.

A pair of primers suitable for use in the practice of the present invention is set forth in SEQ ID NOS 1 and 2. These primers are suitable for use in amplifying genomic DNA encoding alleles of TNF microsatellites a and b, and may be used as a pair or each in combination with another suitable primer. SEQ ID NO 1 is complementary to DNA downstream of the TNF microsatellite b locus, as depicted in FIG. 1. SEQ ID NO 2 is complementary to DNA upstream of the TNF microsatellite a locus, as depicted in FIG. 1.

Alternatively, it may be desirable to amplify nucleic acid encoding the alleles of TNF microsatellite a or b separately. In that case, for example SEQ ID NOS 2 and 3 can be used as primer pairs to amplify nucleic acid encoding TNF microsatellite a alleles, while SEQ ID NO 1 and 4 can be used as primer pairs to amplify nucleic acid encoding TNF microsatellite a alleles. See FIG. 1 for the relative location and orientation of primers with regard to TNF microsatellite loci.

SEQ ID NOS 5 and 6 encode a pair of primers suitable for use in the amplification of genomic DNA encoding alleles of the TNF microsatellite c and may be used as a pair or each in combination with another suitable primer. As depicted in FIG. 1, SEQ ID NO. 5 is complementary to DNA located downstream of the TNF microsatellite c locus and SEQ ID NO. 6 is complementary of DNA located upstream of the TNF microsatellite c locus.

A pair of primers suitable for use in the practice of the present invention is also set forth in SEQ ID NOS 7 and 10. These primers are suitable for use in amplifying genomic DNA encoding alleles of TNF microsatellites d and e, and may be used as a pair or each in combination with another suitable primer. SEQ ID NO 7 is complementary to DNA downstream of the TNF microsatellite d locus, as depicted in FIG. 1. SEQ ID NO 10 is complementary to DNA upstream of the TNF microsatellite e locus, as depicted in FIG. 1. If one desires to amplify nucleic acid encoding the alleles of TNF microsatellite d or e separately, SEQ ID NOS 7 and 8 can be used as primer pairs to amplify nucleic acid encoding TNF microsatellite d alleles, while SEQ ID NO 9 and 10 can be used as primer pairs to amplify nucleic acid encoding TNF microsatellite e alleles. See FIG. 1 for the relative location and orientation of these primers with regard to TNF microsatellite loci.

In another embodiment of the present invention, there is provided a method of distinguishing CD from UC comprising detecting the presence or absence of nucleic acid of a subject encoding TNF microsatellite alleles associated with CD, wherein the presence of nucleic acid encoding the a2, b1 and c2 TNF microsatellite alleles is indicative of CD and the absence of the a2, b1 and c2 TNF microsatellite alleles is indicative of UC.

In yet another embodiment of the present invention, there is provided a method of screening for CD comprising determining the TNF microsatellite alleles encoded by nucleic acid of a subject at TNF microsatellite loci selected from the group consisting of a, b, c, d and e and identifying CD by the presence of three or more TNF microsatellite alleles selected from the group consisting of a2, b1, c2, d4 and e1.

The novel methods for screening for CD and for distinguishing CD from UC disclosed herein include the use of traditional diagnostic tests for CD in combination with the detection of nucleic acid of a subject encoding TNF microsatellite alleles associated with CD. Thus, for example, an endoscopic examination which reveals linear or serpiginous ulcerations of the mucosa, a negative ANCA status, or a positive test for HLA DR1 and/or HLA DRQ may be used in combination with detecting the presence of nucleic acid encoding, for example, the a2, b1 and c2 TNF microsatellite alleles, to further indicate CD.

Kits for use in screening for CD and distinguishing CD from UC are also provided by the present invention. Such kits can include all or some of the positive controls, negative controls, reagents, primers, sequencing markers, probes and antibodies described herein for determining the presence or absence of nucleic acid encoding TNF microsatellite alleles associated with CD. Kits of the present invention may contain, for example, nucleic acid encoding TNF microsatellite alleles associated with CD, nucleic acid encoding TNF microsatellite alleles not known to be associated with CD, the nucleic acid sequence of TNF microsatellite alleles, schedules of the number and type of dinucleotide sequence repeats characteristic of each TNF microsatellite allele, one or more labeled oligonucleotide probes specific for particular TNF microsatellite alleles, one or more primers for amplification of nucleic acid encoding TNF microsatellite alleles, reagents commonly used for amplification, polymerase, antibody specific for, or which binds particular TNF microsatellite alleles and combinations of any of the above.

As amenable, these suggested kit components may be packaged in a manner customary for use by those of skill in the art. For example, these suggested kit components may be provided in solution or as a liquid dispersion or the like.

A presently preferred embodiment of the inventive kits for use in screening for CD or distinguishing CD from UC comprises DNA encoding two or more TNF microsatellite alleles associated with CD in Tris-EDTA buffer solution preferably kept at 4° C. or lyophilized, for example, TNF microsatellite alleles selected from a group comprising the a2, b1, c2, d4 and e1 TNF microsatellite alleles.

Another embodiment of the inventive kits for use in screening for CD or distinguishing CD from UC further comprises one or more primers specific for amplification of nucleic acid encoding TNF microsatellite alleles, for example, primers selected from the comprising SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9 and SEQ ID NO 10.

Yet another embodiment of the inventive kits for use in screening for CD or distinguishing CD from UC further comprises sequencing markers ranging in size from about 80 to 200 base pairs.

The invention will now be described in greater detail by reference to the following non-limiting examples.

A. EXAMPLES

1. Subjects Tested To Identify TNF Microsatellite Allele Associated with CD

A total of 73 UC patients and 75 CD patients were involved. To select an ethnically, socioeconomically matched control group for the association study, 60 people were chosen from the spouses or acquaintances of the patients. An individual was used as control only if he/she did not have inflammatory bowel disease, multiple sclerosis, systemic lupus erythematosus, or other recognized autoimmune diseases. The distribution of age, gender, and ethnicity (Jewish/non-Jewish) were comparable between patients and controls. All patients and controls analyzed are Caucasians. Genomic DNA was isolated from peripheral blood mononuclear cells of the patients and the control group.

2. Amplification of Nucleic Acid Encoding TNF Microsatellites by PCR

PCR was performed on a Perkin-Elmer 480 PCR machine. Genomic DNA encoding TNF microsatellite can be amplified using a two-stage PCR amplification. In the first stage, three separate PCR reactions are performed. One PCR reaction uses SEQ ID NOS. 1 and 2 as primers to amplify nucleic acid encoding TNF microsatellites a and b as one sequence. A second PCR reaction uses SEQ ID NOS. 5 and 6 as primers to amplify nucleic acid encoding TNF microsatellite c as a separate sequence. And, a third PCR reaction uses SEQ ID NOS. 7 and 10 as primers to amplify nucleic acid encoding TNF microsatellites d and e as a third sequence. Each of these three PCR reactions in the first PCR stage are performed in a total volume of 20 $\mu$l with 10 mM Tris-HCl (pH 8.3), 50 mM KCl, 2 mM $MgCl_2$, 0.15 $\mu$M primers, 200 $\mu$M each dATP, dCTP, dGTP, dTTP; 100 to 300 ng genomic DNA, and 1 unit Taq DNA polymerase.

PCR conditions were as follows: Initial denaturing of nucleic acid sample at 94° C. for 7 minutes, followed by a second denaturing at 94° C. for 60 sec., followed by annealing primers at 60° C. for 60 sec., and amplification. at 72° C. for 60 sec. for 25 cycles. This is followed by a 5 minute extension at 72° C.

In the second stage of the two-stage PCR amplification, DNA fragments for each loci are amplified separately. Two $\mu$l of the first PCR reaction are added to the same reagents at the same concentrations as were used in the first stage of PCR to a total volume of 20 $\mu$l., except that instead of using dATP, the second stage PCR reactions were carried out in the presence of 5 µCi³⁵S-α-dATP and the following primers were used: to amplify nucleic acid encoding TNF microsatellite a, SEQ ID NOS. 2 and 3 were used as primers; to amplify nucleic acid encoding TNF microsatellite b, SEQ ID NOS. 1 and 4 were used as primers; to amplify nucleic acid encoding TNF microsatellite c, SEQ ID NOS. 5 and 6 were again used as primers; to amplify nucleic acid encoding TNF microsatellite d, SEQ ID NOS. 7 and 8 were used as primers; and to amplify nucleic acid encoding TNF microsatellite e, SEQ ID NOS. 9 and 10 were used as primers. Six cycles of PCR are completed as described above, followed by a 5 minute extension at 72° C. After the second round of amplification, 3 µl of product are mixed with 3 µl of a formamide stop solution.

3. Electrophoresis of Amplified Nucleic Acid Encoding TNF Microsatellites

Four to 5 µl amplified DNA are electrophoresed on a 7 M urea, 5% polyacrylamide, 0.4 mm sequencing gel. Gels are dried and autoradiographed for 48 to 72 hours. Gels are run with a pGEM-3Zs(+) control DNA sequencing marker available form Promega of Madison, Wis., to size fragments. Although extra fragments may shadow the specific DNA bands, results are unambiguously interpretable, and confirmed by comparison to nucleic acid derived from the cell lines having the specified TNF microsatellite alleles set forth in Table 4 and subjected to the same amplification and electrophoresis procedures described above.

TABLE 4

Cell lines providing a source of positive and negative control DNA for detecting the presence or absence of TNF microsatellite alleles associated with CD.

| NAME | ASHI NO. | CEPH NO. | ENCODED TNF MICROSATELLITE ALLELES |
|---|---|---|---|
| BM1 | 9038 | ws57 | a10, b4, c1, d3 and e3 |
| OBL | 9020 | ws71 | a1, b5, c2, d4, and e3 |
| TAB 089 | 9066 | ws32 | a6, b5, c1, d7, and e4 |
| COX | 9022 | ws13 | a3, b3, c1, d3, and e3 |
| BSM | 9032 | ws68 | a2, b1, c2, d4, and e1 |
| OLGA | 9071 | ws36 | a6, b5, c1, d5, and e3 |

Although the invention has been described with reference to presently preferred embodiments, it should be understood that various modifications can be made without departing from the spirit of the invention.

We claim:

1. A method of screening for Crohn's disease in an inflammatory bowel disease patient, comprising detecting in said inflammatory bowel disease patient the presence or absence of TNF microsatellite alleles a2, b1 and c2, wherein the presence of said TNF microsatellite alleles a2, b1, and c2 indicates that said patient has Crohn's disease.

2. The method of claim 1, wherein detection comprises amplifying the nucleic acid and identifying the TNF microsatellite alleles.

3. The method of claim 2, wherein identification comprises subjecting the amplified nucleic acid to electrophoresis and comparing the results to a positive control.

4. The method of claim 3, wherein identification further comprises comparing the results of electrophoresis to a negative control.

5. The method of claim 2, wherein amplification comprises use of one or more primers specific for amplification of nucleic acid encoding TNF microsatellite alleles.

6. The method of claim 5, wherein at least one primer is selected from the group consisting of SEQ ID NO 1, SEQ ID NO 2, SEQ ID NO 3, SEQ ID NO 4, SEQ ID NO 5, and SEQ ID NO 6.

7. The method of claim 5, wherein at least one primer is selected from the group consisting of SEQ ID NO 1, SEQ ID NO 2, SEQ ID NO 5, and SEQ ID NO 6.

8. The method of claim 1, wherein detection comprises sequencing the nucleic acid encoding TNF microsatellite alleles and identifying the TNF microsatellite alleles.

9. The method of claim 1, further comprising detecting in said inflammatory bowel disease patient the presence or absence of a TNF microsatellite allele selected from the group consisting of d4 and e1, wherein the presence of TNF microsatellite alleles a2, b1, c2 and d4 or TNF microsatellite alleles a2, b1, c2 and e1 is indicative of Crohn's disease.

10. The method of claim 9, comprising detecting in said inflammatory bowel disease patient the presence or absence of TNF microsatellite allele d4, wherein the presence of TNF microsatellite alleles a2, b1, c2 and d4 is indicative of Crohn's disease.

11. The method of claim 9, comprising detecting in said inflammatory bowel disease patient the presence or absence of TNF microsatellite allele e1, wherein the presence of TNF microsatellite alleles a2, b1, c2 and e1 is indicative of Crohn's disease.

* * * * *

SEQUENCE LISTING

```
<160> NUMBER OF SEQ ID NOS:  10

<210> SEQ ID NO 1
<211> LENGTH: 22
<212> TYPE: DNA
<213> ORGANISM: Homo sapiens
<220> FEATURE:
<223> OTHER INFORMATION: (genomic)

<400> SEQUENCE: 1
gcactccagc ctaggccaca ga                                             22

<210> SEQ ID NO 2
<211> LENGTH: 24
<212> TYPE: DNA
<213> ORGANISM: Homo sapiens
<220> FEATURE:
<223> OTHER INFORMATION: (genomic)

<400> SEQUENCE: 2
gcctctagat ttcatccagc caca                                           24

<210> SEQ ID NO 3
<211> LENGTH: 22
<212> TYPE: DNA
<213> ORGANISM: Homo sapiens
<220> FEATURE:
<223> OTHER INFORMATION: (genomic)

<400> SEQUENCE: 3
cctctctccc ctgcaacaca ca                                             22

<210> SEQ ID NO 4
<211> LENGTH: 22
<212> TYPE: DNA
<213> ORGANISM: Homo sapiens
<220> FEATURE:
<223> OTHER INFORMATION: (genomic)
```

```
<400> SEQUENCE: 4
gtgtgtgttg cagggagag ag                                             22

<210> SEQ ID NO 5
<211> LENGTH: 24
<212> TYPE: DNA
<213> ORGANISM: Homo sapiens
<220> FEATURE:
<223> OTHER INFORMATION: (genomic)

<400> SEQUENCE: 5
ggtttctctg actgcatctt gtcc                                          24

<210> SEQ ID NO 6
<211> LENGTH: 23
<212> TYPE: DNA
<213> ORGANISM: Homo sapiens
<220> FEATURE:
<223> OTHER INFORMATION: (genomic)

<400> SEQUENCE: 6
tcatggggag aacctgcaga gaa                                           23

<210> SEQ ID NO 7
<211> LENGTH: 24
<212> TYPE: DNA
<213> ORGANISM: Homo sapiens
<220> FEATURE:
<223> OTHER INFORMATION: (genomic)

<400> SEQUENCE: 7
agatccttcc ctgtgagttc tgct                                          24

<210> SEQ ID NO 8
<211> LENGTH: 24
<212> TYPE: DNA
<213> ORGANISM: Homo sapines
<220> FEATURE:
<223> OTHER INFORMATION: (genomic)

<400> SEQUENCE: 8
catagtggga ctctgtctcc aaag                                          24

<210> SEQ ID NO 9
<211> LENGTH: 22
<212> TYPE: DNA
<213> ORGANISM: Homo sapiens
<220> FEATURE:
<223> OTHER INFORMATION: (genomic)

<400> SEQUENCE: 9
gtgcctggtt ctggagcctc tc                                            22

<210> SEQ ID NO 10
<211> LENGTH: 24
<212> TYPE: DNA
<213> ORGANISM: Homo sapiens
<220> FEATURE:
<223> OTHER INFORMATION: (genomic)

<400> SEQUENCE: 10
tgagacagag gataggagag acag                                          24
```